United States Patent [19]

Shannon et al.

[11] Patent Number: 4,767,840
[45] Date of Patent: Aug. 30, 1988

[54] CYCLIC MONOCARBONATE BISHALOFORMATES, METHOD FOR THEIR PREPARATION, AND USES THEREOF

[75] Inventors: Thomas G. Shannon, Schenectady; Daniel J. Brunelle, Scotia, both of N.Y.

[73] Assignee: General Electric Company, Schenectady, N.Y.

[21] Appl. No.: 29,515

[22] Filed: Mar. 24, 1987

[51] Int. Cl.$^4$ .............................................. C08L 69/00
[52] U.S. Cl. .................................. 528/196; 528/202; 528/370; 528/372; 525/461; 549/228
[58] Field of Search ............... 528/196, 202, 370, 372; 549/228; 525/461

[56] References Cited

U.S. PATENT DOCUMENTS 4,568,755  2/1986  Mues et al. ..................... 549/228

Primary Examiner—Theodore E. Pertilla
Attorney, Agent, or Firm—William H. Pittman; James C. Davis, Jr.; James Magee, Jr.

[57] ABSTRACT

Cyclic monocarbonate bischloroformates are prepared by the reaction of a carbonyl halide such as phosgene with a bridged substituted resorcinol or hydroquinone such as bis(2,4-dihydroxy-3-methylphenyl)methane or bis(2,5-dihydroxy-3,4,6-trimethylphenyl)methane in the presence of aqueous alkali metal hydroxide. The cyclic monocarbonate bischloroformates may be used for the preparation of linear or cyclic polycarbonates containing cyclic carbonate structural units, which may in turn be converted to crosslinked polycarbonates.

10 Claims, No Drawings

CYCLIC MONOCARBONATE BISHALOFORMATES, METHOD FOR THEIR PREPARATION, AND USES THEREOF

This invention relates to crosslinked polycarbonates and precursors therefor. More particularly, it relates to monocarbonate bishaloformates suitable for polycarbonate crosslinking.

Polycarbonates are well known polymers which have good property profiles, particularly with respect to impact resistance, electrical properties, optical clarity, dimensional rigidity and the like. These polymers are generally linear, but can be made with branched sites to enhance their properties in specific ways. Low levels of branching are generally incorporated into the resin by copolymerizing into the polymer backbone a polyfunctional reagent to yield a thermoplastic polycarbonate resin with enhanced rheological properties and melt strength which make it particularly suitable for such types of polymer processing procedures as the blow molding of large, hollow containers and the extrusion of complex profile forms. Special manufacturing runs must be set aside to prepare these branched polycarbonate resins.

Sufficiently higher levels of branching sites in the resin will cause resin chains actually to join to each other to form partially or fully crosslinked resin networks which will no longer be thermoplastic in nature and which are expected to exhibit enhancements over corresponding linear resins in physical properties and/or in their resistance to abusive conditions, such as exposure to organic solvents. A wide variety of means have been employed to produce crosslinking in polycarbonate resins. They generally involve the incorporation of a suitably reactive chemical group into the resin chain at its time of manufacture, as an additive to the resin after manufacture, or both. These reactive groups and the reactions they undergo are generally different from those characteristic of polycarbonate resins themselves and therefore tend to have detrimental side effects on the physical and/or chemical properties of the polymer. The conventional test used to judge the success of these means for crosslinking is to observe the formation of gels due to the crosslinked material when a resin sample is mixed with a solvent, such as methylene chloride, in which normal linear polycarbonate resin is highly soluble.

By the present invention, compounds are provided which may be incorporated in conventional polycarbonate reaction mixtures to provide carbonate groups as branching or crosslinking sites in the polymers. (For brevity, the term "crosslinking" as used hereinafter will denote both branching and crosslinking.) Said compounds are suitable for incorporation either in linear or cyclic polycarbonate reaction mixtures. There are also provided linear and cyclic polycarbonates prepared by such reactions, as well as related crosslinked polycarbonates.

In one of its aspects, the present invention include cyclic monocarbonate bishaloformates having the formula

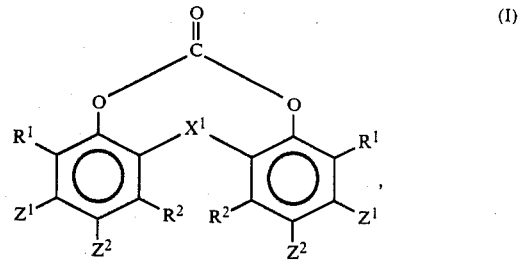

wherein:
$X^1$ is $R^3CH$, S, SO or $SO_2$;
$R^1$ is $C_{1-4}$ alkyl or halo;
$R^2$ is hydrogen, $C_{1-4}$ alkyl or halo;
$R^3$ is hydrogen or an alkyl, cycloalkyl or aryl Radical;
one of $Z^1$ and $Z^2$ is hydrogen, $C_{1-4}$ alkyl or halo and the other is

and $X^2$ is chlorine or bromine.

The $R^1$ groups in the monocarbonate bishaloformates of this invention may be $C_{1-4}$ alkyl groups such as methyl, ethyl, n-propyl, isopropyl, n-butyl or t-butyl, or halogen atoms such as chlorine and bromine. The presence of a relatively bulky substituent of this type is critical to avoid condensation of the haloformate groups to carbonate groups, which is frequently accompanied by formation of gel in large amounts. Methyl groups (especially) and chlorine and bromine atoms are preferred. The $R^2$ groups may be hydrogen or alkyl or halo groups similar to $R^1$.

The linking $X^1$ radical may be methylene, substituted methylene, sulfur, sulfoxy or sulfone, wherein the $R^3$ substituents on any substituted methylene radicals may be alkyl, cycloalkyl or aryl. Most often, such substituents contain up to about 7 carbon atoms. Unsubstituted methylene is frequently preferred.

Of the $Z^1$ and $Z^2$ values, one must be

wherein $X^2$ is chlorine or bromine and is preferably chlorine, and the other must be hydrogen, alkyl or halo as defined for $R^2$. Thus, the monocarbonate bishaloformates of the invention may be considered as being derived from bridged substituted resorcinols and hydroquinones of the formulas

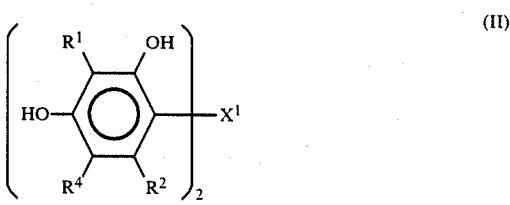

and

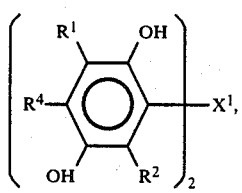
(III)

respectively, wherein $R^4$ is hydrogen, $C_{1-4}$ alkyl or halo as previously defined for $R^2$.

The cyclic monocarbonate bishaloformates of this invention may be prepared by reacting a bridged substituted resorcinol or hydroquinone of formula II or III with a stoichiometric excess of a carbonyl halide of the formula $CO(X^2)_2$ (i.e., phosgene or carbonyl bromide) in the presence of an aqueous alkali metal hydroxide solution. This reaction, which is another aspect of the invention, is typically conducted at a temperature in the range of about 0°–35° C.

The bridged substituted resorcinols and hydroquinones may be prepared by known methods, such as the reaction of the corresponding dihydroxyaromatic compounds (e.g., 2-methylresorcinol or trimethylhydroquinone) with formaldehyde or sulfur dichloride, followed when appropriate by oxidation of divalent sulfur to a sulfoxide or sulfone group. The preparation of sulfur- and sulfoxy-bridged compounds is disclosed, for example, in U.S. Pat. Nos. 3,857,896 and 3,881,931, and of methylene-bridged compounds in copending, commonly owned application Serial Nb. 913,908, filed Oct. 1, 1986, the disclosures of which are incorporated by reference herein. The following example illustrates the preparation of methylene-bridged compounds.

EXAMPLE 1

To a solution of 248.14 parts by weight (2 moles) of 2-methylresorcinol in one liter of 2 M aqueous hydrochloric acid was added 32.6 parts of 38% aqueous formaldehyde solution (0.4 mole of formaldehyde). The mixture was stirred for two hours at about 20° C., whereupon a white solid precipitated. It was removed by filtration, washed several times with water and dried. The product was shown by infrared and nuclear magnetic resonance spectroscopy to be the desired bis(2,4-dihydroxy-3-methylphenyl)methane. The yield was 49.2 parts, or 50% of theoretical.

In one embodiment of the method for preparing cyclic monocarbonate bishaloformates, gaseous phosgene is passed into a solution of the bridged substituted resorcinol or hydroquinone in a substantially non-polar organic liquid which forms a two-phase system with water. The identity of the liquid is not critical, provided it possesses the stated properties. Illustrative liquids are aromatic hydrocarbons such as toluene and xylene; substituted aromatic hydrocarbons such as chlorobenzene, o-dichlorobenzene and nitrobenzene; chlorinated aliphatic hydrocarbons such as chloroform and methylene chloride; and mixtures of the foregoing with ethers such as tetrahydrofuran. Methylene chloride is frequently preferred.

Phosgene passage in this embodiment is generally at a temperature of about 10°–35° C. and preferably at about room temperature. There is simultaneously added an aqueous alkali metal hydroxide solution (e.g., sodium hydroxide or potassium hydroxide, with sodium hydroxide being preferred) having a concentration in the range of about 2–10M. The addition rate of the alkali metal hydroxide is adjusted so as to provide a pH in the range of about 3–9.

A second embodiment is to condense phosgene with the solution of the bridged substituted resorcinol or hydroquinone at a temperature below the condensation temperature of phosgene, typically about 0° C., and subsequently to add sodium hydroxide while warming the mixture to effect reflux of phosgene. In either procedure, the amount of phosgene employed is about a 20–100% excess over the stoichiometric amount of 3 moles per mole of bridged substituted resorcinol or hydroquinone required for formation of the monocarbonate bishaloformate.

Following the reaction, excess phosgene is ordinarily removed by conventional means such as nitrogen purging. The cyclic monocarbonate bishaloformate may then be dried and isolated, also by conventional means.

The preparation of the cyclic monocarbonate bishaloformates of this invention is illustrated by the following examples.

EXAMPLE 2

A mixture of 50 ml. of methylene chloride and 2 grams (7.7 mmol.) of bis(2,4-dihydroxy-3-methylphenyl)methane was cooled in an ice bath to 0° C. and 4.6 grams (45 mmol.) of phosgene was added. The mixture was allowed to warm to room temperature, with stirring, over 15 minutes as 125 mmol. of 5M aqueous sodium hydroxide solution was added. Phosgene reflux was maintained by use of a condenser containing solid carbon dioxide and acetone.

When sodium hydroxide addition was complete, stirring was continued for 10 minutes at room temperature after which excess phosgene was removed by purging with nitrogen. The organic layer was separated, washed three times with dilute aqueous hydrochloric acid solution, dried with phase separation paper and vacuum stripped to yield 2.27 grams (72% of theoretical) of the desired cyclic monocarbonate bischloroformate as a tan solid. The molecular structure of the product was confirmed by proton nuclear magnetic resonance spectroscopy and field desorption mass spectroscopy.

EXAMPLE 3

Phosgene, 10 grams (100 mmol.), was passed at 0.5 gram per minute, with stirring, into a solution of 6.32 grams (20 mmol.) of bis(2,5-dihydroxy-3,4,6-trimethylphenyl)methane in 100 ml. of methylene chloride. There was simultaneously added a 5M aqueous sodium hydroxide solution at a rate to maintain the pH in the range of 4–9. Stirring was continued for 15 minutes after phosgene addition was complete, after which excess phosgene was removed by nitrogen purging. Upon workup as described in Example 2, there was obtained 5.75 grams (62% of theoretical) of the desired cyclic monocarbonate bischloroformate. Its structure was confirmed by reaction with methanol in the presence of triethylamine to yield the corresponding bis(methyl carbonate), followed by proton nuclear magnetic resonance spectroscopy.

The cyclic monocarbonate bishaloformates of this invention may be homopolymerized or incorporated in conventional reaction mixtures for the preparation of linear or cyclic polycarbonates. The resulting products are polycarbonates comprising cyclic carbonate structural units of the formula

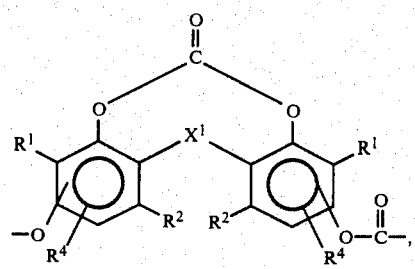

optionally in combination with units of the formula

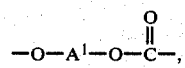

wherein $A^1$ is a divalent aromatic radical and $R^1$, $R^2$, $R^4$ and $X^1$ are as previously defined. These polycarbonates are another aspect of the invention.

In formula IV, the carbonate oxygen atoms and $R^4$ radicals are linked to the aromatic rings in positions corresponding to those in formulas II and III. That is, one of the two in each ring is in the meta-position to the cyclic carbonate oxygen atom and the other is in the para-position thereto.

As previously noted, the $A^1$ values are divalent aromatic radicals. They preferably have the formula

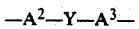

wherein each of $A^2$ and $A^3$ is a monocyclic divalent aromatic radical and Y is a bridging radical in which one or two atoms separate $A^2$ from $A^3$. The free valence bonds in formula II are usually in the meta or para positions of $A^1$ and $A^2$ in relation to Y.

In formula VI, the $A^2$ and $A^3$ values may be unsubstituted phenylene or substituted derivatives thereof, illustrative substituents (one or more) being alkyl, alkenyl, halo (especially chloro and/or bromo), nitro, alkoxy and the like. Unsubstituted phenylene radicals are preferred. Both $A^2$ and $A^3$ are preferably p-phenylene, although both may be o- or m-phenylene or one o- or m-phenylene and the other p-phenylene.

The bridging radical, Y, is one in which one or two atoms, preferably one, separate $A^2$ from $A^3$. It is most often a hydrocarbon radical and particularly a saturated radical such as methylene, cyclohexylmethylene, 2-[2.2.1]-bicycloheptylmethylene, ethylene, isopropylidene, neopentylidene, cyclohexylidene, cyclopentadecylidene, cyclododecylidene or adamantylidene, especially a gemalkylene (alkylidene) radical. Also included, however, are unsaturated radicals and radicals which contain atoms other than carbon and hydrogen; for example, 2,2-dichloroethylidene, carbonyl, phthalidylidene, oxy, thio, sulfoxy and sulfone.

The $A^1$ values may be considered as being derived from dihydroxyaromatic compounds of the formula HO—$A^1$—OH, preferably bisphenols of the formula HO—$A^2$—Y—$A^3$—OH. The following dihydroxy compounds are illustrative:
Resorcinol
4-Bromoresorcinol
Hydroquinone
4,4'-Dihydroxybiphenyl
1,6-Dihydroxynaphthalene
2,6-Dihydroxynaphthalene
Bis(4-hydroxyphenyl)methane
Bis(4-hydroxyphenyl)diphenylmethane
Bis(4-hydroxyphenyl)-1-naphthylmethane
1,1-Bis(4-hydroxyphenyl)ethane
1,2-Bis(4-hydroxyphenyl)ethane
1,1-Bis(4-hydroxyphenyl)-1-phenylethane
2,2-Bis(4-hydroxyphenyl)propane ("bisphenol A")
2-(4-Hydroxyphenyl)-2-(3-hydroxyphenyl) propane
2,2-Bis(4-hydroxyphenyl)butane
1,1-Bis(4-hydroxyphenyl)isobutane
1,1-Bis(4-hydroxyphenyl)cyclohexane
1,1-Bis(4-hydroxyphenyl)cyclododecane
Trans-2,3-bis(4-hydroxyphenyl)-2-butene
2,2-Bis(4-hydroxyphenyl)adamantane
α,α'-Bis(4-hydroxyphenyl)toluene
Bis(4-hydroxyphenyl)acetonitrile
2,2-Bis(3-methyl-4-hydroxyphenyl)propane
2,2-Bis(3-ethyl-4-hydroxyphenyl)propane
2,2-Bis(3-n-propyl-4-hydroxyphenyl)propane
2,2-Bis(3-isopropyl-4-hydroxyphenyl)propane
2,2-Bis(3-sec-butyl-4-hydroxyphenyl)propane
2,2-Bis(3-t-butyl-4-hydroxyphenyl)propane
2,2-Bis(3-cyclohexyl-4-hydroxyphenyl)propane
2,2-Bis(3-allyl-4-hydroxyphenyl)propane
2,2-Bis(3-methoxy-4-hydroxyphenyl)propane
2,2-Bis(3,5-dimethyl-4-hydroxyphenyl)propane
2,2-Bis(2,3,5,6-tetramethyl-4-hydroxyphenyl)propane
2,2-Bis(3,5-dichloro-4-hydroxyphenyl)propane
2,2-Bis(3,5-dibromo-4-hydroxyphenyl)propane
2,2-Bis(2,6-dibromo-3,5-dimethyl-4-hydroxyphenyl)propane
αα-Bis(4-hydroxyphenyl)toluene
α,α,α',α'-Tetramethyl-α,α'-bis(4-hydroxyphenyl)-p-xylene
2,2-Bis(4-hydroxyphenyl)hexafluoropropane
1,1-Dichloro-2,2-bis(4-hydroxyphenyl)ethylene
1,1-Dibromo-2,2-bis(4-hydroxyphenyl)ethylene
1,1-Dichloro-2,2-bis(5-phenoxy-4-hydroxyphenyl)ethylene
4,4'-Dihydroxybenzophenone
3,3-Bis(4-hydroxyphenyl)-2-butanone
1,6-Bis(4-hydroxyphenyl)-1,6-hexanedione
Ethylene glycol bis(4-hydroxyphenyl) ether
Bis(4-hydroxyphenyl) ether
Bis(4-hydroxyphenyl) sulfide
Bis(4-hydroxyphenyl) sulfoxide
Bis(4-hydroxyphenyl) sulfone
Bis(3,5-dimethyl-4-hydroxyphenyl) sulfone
9,9-Bis(4-hydroxyphenyl)fluorene
2,7-Dihydroxypyrene
6,6'-Dihydroxy-3,3,3',3'-tetramethylspiro(bis)indane ("spirobiindane bisphenol")
3,3-Bis(4-hydroxyphenyl)phthalide
2,6-Dihydroxydibenzo-p-dioxin
2,6-Dihydroxythianthrene
2,7-Dihydroxyphenoxathiin
2,7-Dihydroxy-9,10-dimethylphenazine
3,6-Dihydroxydibenzofuran
3,6-Dihydroxydibenzothiophene
2,7-Dihydroxycarbazole.

Bisphenol A is often preferred for reasons of availability and particular suitability for the purposes of the invention.

The polycarbonates of this invention include linear polycarbonates. They may be prepared by employing the cyclic monocarbonate bishaloformates of the invention in conventional polycarbonate-forming reactions.

For example, the cyclic monocarbonate bishaloformate may be added concurrently with phosgene to a heterogeneous mixture including a bisphenol solution, whereupon both the phosgene and the cyclic monocarbonate bishaloformate will react with the bisphenol to form a linear polycarbonate. Preferably, however, the cyclic monocarbonate bishaloformate is combined with a bishaloformate of one of the previously defined dihydroxyaromatic compounds for conversion to polycarbonates by the action of an interfacial polycarbonate formation catalyst and an acid acceptor, according to general methods known in the art. Reference is made, for example, to U.S. Pat. Nos. 3,189,640 and 4,025,489, as well as copending, commonly owned application Ser. No. 917,751, filed Oct. 10, 1986, now U.S. Pat. No. 4,737,573, the disclosures of which are incorporated by reference herein.

Another species of polycarbonates of this invention consists of cyclic polycarbonate oligomers. These may be single oligomeric compounds such as those disclosed in the following U.S. patents:

| | |
|---|---|
| 3,155,683 | 3,386,954 |
| 3,274,214 | 3,422,119. |

Cyclic polycarbonate oligomer mixtures may also be prepared. Mixtures of this type are disclosed in U.S. Pat. No. 4,644,053, the disclosure of which is incorporated by reference herein.

The cyclic oligomer mixtures consist essentially of oligomers having degrees of polymerization from 2 to about 30 and preferably to about 20, with a major proportion being up to about 12 and a still larger proportion up to about 15. Since they are mixtures of oligomers having varying degrees of polymerization, these compositions have relatively low melting points as compared to single compounds. The cyclic oligomer mixtures are generally liquid at temperatures above 300° C. and most often at temperatures above 225° C.

It has been discovered that the cyclic oligomer mixtures contain very low proportions of linear oligomers. In general, no more than about 10% by weight, and most often no more than about 5% (if any), of such linear oligomers are present. The mixtures also usually contain at most low percentages (frequently less than 30% and preferably no higher than about 20%) of polymers (linear or cyclic) having a degree of polymerization greater than about 30. Such polymers are frequently identified hereinafter as "high polymer". These properties, coupled with the relatively low melting points and viscosities of the cyclic oligomer mixtures, contribute to their utility as resin precursors, especially for high molecular weight resins.

The cyclic oligomer mixtures of this invention may be prepared by a method which comprises contacting (A) a composition comprising at least one cyclic monocarbonate bishaloformate of formula I with (B) at least one oleophilic aliphatic or heterocyclic tertiary amine and (C) an aqueous alkali or alkaline earth metal hydroxide or carbonate solution;

said contact being effected under conditions whereby reagent A is maintained in low concentration in (D) a substantially non-polar organic liquid which forms a two-phase system with water.

Reagent A comprises (1) at least one cyclic monocarbonate bishaloformate of the invention (reagent A-1).

It may also contain (2) at least one bishaloformate of the formula $$A^1(OCOX^2)_2 \qquad (VII)$$

wherein $A^1$ and $X^2$ are as defined hereinabove (reagent A-2), and, optionally, (3) at least one diol having the formula $$R^5(OH)_2 \qquad (VIII)$$

wherein $R^5$ is a divalent aliphatic or alicyclic radical, or an alkali metal salt thereof (reagent A-3), as well as other compounds, including bishaloformate oligomers. The proportion of cyclic monocarbonate bishaloformate in admixture with such other compounds will depend on the amount of crosslinking desired in the final linear polycarbonate, and is generally at least about 1 and preferably about 2–10 mole percent.

While the $X^2$ values in formulas I and VII may be chlorine or bromine, the bischloroformates, in which $X^2$ is chlorine, are most readily available and their use is therefore preferred. (Frequent reference to bischloroformates will be made hereinafter, but it should be understood that other bishaloformates may be substituted therefor as appropriate.) Suitable bis(active hydrogen) compounds of formula VIII (reagent A-3) include dihydroxyaromatic compounds having divalent radicals which are identical to or different from the corresponding divalent radicals in the compound of formula VII, as well as other diols. When such diols (or their alkali metal salts) are present, they generally comprise up to about 50%, most often up to about 20% and preferably up to about 10%, of the total of reagents A-2 and A-3.

Most preferably, reagent A consists essentially of reagents A-1 and A-2 or of a mixture of reagent A-1 and reagents A-2 and A-3 in which $A^1$ and $R^5$ are identical, as noted hereinafter. Any cyclic oligomers containing divalent aliphatic radicals or their vinylogs are prepared by using a mixture of compounds identifiable as reagent A-2.

Reagent A-2 may be a bischloroformate in substantially pure, isolated form. It is frequently preferred, however, to use a crude bischloroformate product. Suitable crude products may be prepared by any known methods for bischloroformate preparation. Typically, at least one bisphenol is reacted with phosgene in the presence of a substantially inert organic liquid, as disclosed in the following U.S. patents:

| | |
|---|---|
| 3,255,230 | 3,966,785 |
| 3,312,661 | 3,974,126. |

The disclosures of these patents are incorporated by reference herein.

In addition to the bisphenol bischloroformate, such crude bischloroformate products may contain oligomer bischloroformates. Most often, a major proportion of the crude product comprises monomer, dimer and trimer bischloroformate. Higher oligomer bischloroformates, and monochloroformates corresponding to any of the aforementioned bischloroformates, may also be present, preferably only in relatively small amounts.

More preferably, the preparation of the crude bischloroformate product takes place in the presence of aqueous alkali. The pH of the reaction mixture may be up to about 12. It is generally found, however, that the proportion of high polymer in the cyclic oligomer mixture is minimized by employing a crude bischloroformate product comprising a major amount of bisphenol bischloroformate and only minor amounts of any oligomer bischloroformates. Such products may be obtained by the method disclosed in U.S. Pat. No. 4,638,077, the disclosure of which is also incorporated by reference herein. In that method, phosgene is passed into a mixture of a substantially inert organic liquid and a bisphenol, said mixture being maintained at a temperature within the range of about 10°–40° C., the phosgene flow rate being at least 0.15 equivalent per equivalent of bisphenol per minute when the temperature is above 30° C. An aqueous alkali metal or alkaline earth metal base solution is simultaneously introduced as necessary to maintain the pH in the range of about 0.5–8.0. By this method, it is possible to prepare bischloroformate in high yield while using a relatively small proportion of phosgene, typically up to about 1.1 equivalent per equivalent of bisphenol.

When one of these methods is employed, it is obvious that the crude bischloroformate product will ordinarily be obtained as a solution in a substantially non-polar organic liquid such as those disclosed hereinafter. Depending on the method of preparation, it may be desirable to wash said solution with a dilute aqueous acidic solution to remove traces of base used in preparation.

The tertiary amines useful as reagent B ("tertiary" in this context denoting the absence of N-H bonds) generally comprise those which are oleophilic (i.e., which are soluble in and highly active in organic media, especially those used in the oligomer preparation method), and more particularly those which are useful for the formation of polycarbonates. Reference is made, for example, to the tertiary amines disclosed in U.S. Pat. Nos. 4,217,438 and 4,368,315, the disclosures of which are also incorporated by reference herein. They include aliphatic amines such as triethylamine, tri-n-propylamine, diethyl-n-propylamine and tri-n-butylamine and highly nucleophilic heterocyclic amines such as 4-dimethylaminopyridine (which, for the purposes of this invention, contains only one active amine group). The preferred amines are those which dissolve preferentially in the organic phase of the reaction system; that is, for which the organic-aqueous partition coefficient is greater than 1. This is true because intimate contact between the amine and reagent A is essential for the formation of the cyclic oligomer mixture. For the most part, such amines contain at least about 6 and preferably about 6–14 carbon atoms.

The amines most useful as reagent B are trialkylamines containing no branching on the carbon atoms in the 1- and 2-positions. Especially preferred are tri-n-alkylamines in which the alkyl groups contain up to about 4 carbon atoms. Triethylamine is most preferred by reason of its particular availability, low cost, and effectiveness in the preparation of products containing low percentages of linear oligomers and high polymers.

Reagent C is an aqueous alkali or alkaline earth metal hydroxide or carbonate solution, such as lithium, sodium, potassium or calcium hydroxide or sodium or potassium carbonate. It is most often lithium, sodium or potassium hydroxide, with sodium hydroxide being preferred because of its availability and relatively low cost. The concentration of the solution is not critical and may be about 0.1–16M, preferably about 0.1–10M.

The fourth essential component (component D) in the cyclic oligomer preparation method is a substantially non-polar organic liquid which forms a two-phase system with water. Suitable liquids are defined hereinabove with reference to the preparation of cyclic monocarbonate bishaloformates.

To prepare the cyclic oligomer mixture according to the above-described method, the reagents and components are maintained in contact under conditions whereby reagent A is present in low concentration. Actual high dilution conditions, requiring a large proportion of component D, may be employed but are usually not preferred for cost and convenience reasons. Instead, simulated high dilution conditions known to those skilled in the art may be employed. For example, in one embodiment of the method reagent A (and optionally other reagents) are added gradually to a reaction vessel containing solvent.

Although addition of reagent A neat (i.e., without solvents) is within the scope of this embodiment, it is frequently inconvenient because many bischloroformates are solids. Therefore, it is preferably added as a solution in a portion of component D, especially when it consists essentially of reagents A-1 and A-2. The proportion of component D used for this purpose is not critical; about 25–75% by weight, and especially about 40–60%, is preferred.

The reaction temperature is generally in the range of about 0°–50° C. It is most often about 0°–40° C. and preferably 20°–40° C.

For maximization of the yield and purity of cyclic oligomers as opposed to high polymer and insoluble and/or intractable by-products, it is preferred to use not more than about 1.5 mole of reagent A, calculated as bischloroformate (and bisphenol or salt thereof if present), per liter of component D in the reaction system, including any liquid used to dissolve reagent A. Preferably, about 0.003–1.0 mole of reagent A is used when it consists entirely of reagents A-1 and (optionally) A-2 and no more than about 0.5 mole is used when it includes reagent A-3. It should be noted that this is not a molar concentration in component D when reagent A is added gradually, since said reagent is consumed as it is added to the reaction system.

The molar proportions of the reagents constitute another important feature for yield and purity maximization. The preferred molar ratio of reagent B to the total of reagent A-1 and any reagent A-2 (calculated as bischloroformate) is about 0.1–1.0:1 and most often about 0.15–0.6:1, and that of reagent C to the total of reagent A-1 and any reagent A-2 is about 2–5:1 and most often about 4–5:1. When a combination including reagent A-3 is used, the preferred molar ratio for reagent B is about 0.1–0.5:1. The preferred ratio for reagent C is the same as above, including any alkali metal hydroxide used to form an alkali metal salt used as reagent A-3.

The use of reagent A-3 comprising a bisphenol alkali metal salt is of particular value when it is desired to minimize the amount of phosgene required for overall production of cyclic polycarbonates. When reagent A-1 and (optionally) reagent A-2 are used alone, half the phosgene used for bischloroformate formation is lost by hydrolysis upon conversion of the bischloroformate to cyclics. On the other hand, each chloroformate moiety can theoretically react with a bisphenol salt moiety to form a carbonate group if the latter is present in sufficient amount. It is also frequently found that the proportion of cyclic dimer in the product is maximized by use of reagent A-3.

In practice, it is generally found that incorporation of reagent A-3 into cyclics under these conditions is incomplete. Thus, removal of any unreacted bisphenol as its alkali metal salt may be necessary.

Following their preparation, the cyclic oligomers may be separated from at least a portion of the high polymer and insoluble material present. When other reagents are added to reagent C and the preferred conditions and material proportions are otherwise employed, the cyclic oligomer mixture (obtained as a solution in the organic liquid) typically contains less than 30% by weight and frequently less than about 20% of high polymer and insoluble material. When all of the preferred conditions described hereinafter are employed, the product may contain 10% or even less of such material. Depending on the intended use of the cyclic oligomer mixture, the separation step may then be unnecessary.

Therefore, a highly preferred method for preparing the cyclic oligomer mixture comprises the single step of conducting the reaction using as reagent B at least one aliphatic or heterocyclic tertiary amine which, under the reaction conditions, dissolves preferentially in the organic phase of the reaction system, and gradually adding reagent A and at least a portion of reagents B and C simultaneously to a substantially non-polar organic liquid (component D) or to a mixture of said liquid with water, said liquid or mixture being maintained at a temperature in the range of about 0°–50° C.; the amount of reagent A used being up to about 0.7 mole for each liter of component D present in the reaction system, and the total molar proportions of reagents A, B and C being approximately as follows:

B:A—0.06–2.0:1
C:A—4–5:1;

and recovering the cyclic oligomers thus formed.

A factor of some importance in this embodiment is the concentration of available reagent B, which should be maintained at a level as constant as possible during the entire addition period for reagents A-1 and A-2 (if any). If all of reagent B is present in the reaction vessel into which reagents A-1 and (optionally) A-2 are introduced, its concentration steadily decreases, principally by dilution. On the other hand, if reagent B is introduced continuously or in equal increments during introduction of reagents A-1 and (optionally) A-2, its available concentration is initially low and increases more or less steadily during the addition period. These fluctuations can result in a high and constantly varying proportion of high polymer in the product.

When reagent A-3 is employed in this embodiment, cyclics yield is usually optimized if said reagent is absent from the portion of reagent A added near the end of the reaction. In other words, it is often preferred that any batch be terminated by a period of addition of reagent A consisting essentially of reagents A-1 and (optionally) A-2.

It has been found advantageous to introduce reagent B in one initial large portion, usually about 40–95% and preferably about 40–75% by weight of the total amount, followed by incremental or continuous addition of the balance thereof. By this procedure, the concentration of available reagent B is maintained at a fairly constant level in the organic phase during the entire addition period, and it is possible to minimize the proportion of high polymer in the product. Typically, high polymer content is 20% or less when this mode of addition is used.

Under these conditions, it is usually advantageous for the reaction vessel to initially contain about 5–40% and preferably about 5–30% of total reagent C. The balance thereof is also introduced continuously or incrementally. As in the embodiment previously described, another portion of component D may serve as a solvent for reagent A.

Among the other principal advantages of this preferred embodiment are the non-criticality of the degree of dilution of the reagents and the ability to complete the addition and reaction in a relatively short time, regardless of reaction scale. It ordinarily takes only about 25–30 minutes to complete cyclic oligomer preparation by this method, and the cyclic oligomer yield may be 85–90% or more. By contrast, use of a less preferred embodiment may, depending on reaction scale, require an addition period as long as 8–10 hours and the crude product may contain substantial proportions of linear by-products with molecular weights of about 4,000–10,000, which, if not removed, may interfere with subsequent polymerization of the cyclic oligomers by acting as chain transfer agents.

In this preferred embodiment, the pH of the aqueous phase of the reaction mixture is typically in the range of about 9–14 and preferably about 12. When reagent A (and optionally reagent B) is added to all of the reagent C, on the other hand, the initial pH remains on the order of 14 during essentially the entire reaction period.

When separation of impurities is desired, it may be effected by conventional operations such as combining the crude product, as a solid or in solution, with a non-solvent for said impurities. Illustrative non-solvents include ketones such as acetone and methyl isobutyl ketone and esters such as methyl acetate and ethyl acetate. Acetone is a particularly preferred non-solvent.

Recovery of the cyclic oligomers normally means merely separating the same from diluent (by known methods such as vacuum evaporation) and, optionally, from high polymer and other impurities. As previously suggested, the degree of sophistication of recovery will depend on such variables as the intended end use of the product.

The preparation of cyclic polycarbonate oligomer mixtures according to this invention is illustrated by the following example.

EXAMPLE 4

A mixture of 150 ml. of methylene chloride, 62.5 mg. of triethylamine and 2.5 ml. of 5M aqueous sodium hydroxide solution was prepared and there were simultaneously added thereto with stirring, over 35 minutes, a solution of 1 gram (2.45 mmol.) of the cyclic monocarbonate bischloroformate of Example 2 and 17.22 grams (48.78 mmol.) of bisphenol A bischloroformate in 50 ml. of methylene chloride, 47.5 ml. of 5M aqueous sodium hydroxide solution and 1.19 grams (total 12.3 mmol.) of triethylamine. The aqueous and organic phases were separated and the aqueous layer was washed with methylene chloride. The combined organic phases were washed once with dilute aqueous sodium hydroxide, twice with aqueous hydrochloric acid, once again with sodium hydroxide and twice with water, and dried over magnesium sulfate. Upon filtration, vacuum stripping and drying in an oven, there was obtained a white solid which was shown by high pressure liquid chromatography to comprise the desired cyclic oligomer mixture. The yield was about 85%.

The cyclic oligomer compositions of this invention, incorporating units of formula V, may be converted to crosslinked polycarbonates. Accordingly, the present invention includes a method for the preparation of a crosslinked resinous composition which comprises contacting at least one of the previously defined cyclic oligomer compositions with a polycarbonate formation catalyst at a temperature up to about 350° C., as well as crosslinked compositions prepared by said method. The method is similar to that described in the aforementioned U.S. Pat. No. 4,644,053 and in copending, commonly owned application Ser. No. 888,673, filed July 24, 1986, now U.S. Pat. No. 4,740,583, the disclosure of which is incorporated by reference herein. The oligomer compositions may frequently be employed without separation of high polymer therefrom, but if desired, high polymer may be removed as previously described.

The polycarbonate formation catalysts which can be used in the resin formation method of this invention include various bases and Lewis acids. It is known that basic catalysts may be used to prepare polycarbonates by the interfacial method, as well as by transesterification and from cyclic oligomers. Reference is made to the aforementioned U.S. Pat. Nos. 3,155,683, 3,274,214, 4,217,438 and 4,368,315. Such catalysts may also be used to polymerize the cyclic oligomer compositions. Examples thereof are lithium phenoxide, lithium 2,2,2-trifluoroethoxide, n-butyllithium and tetramethylammonium hydroxide. Also useful are various weakly basic salts such as sodium benzoate and lithium stearate.

A particularly useful class of Lewis bases is disclosed in U.S. Pat. No. 4,605,731. It comprises numerous tetraarylborate salts, including lithium tetraphenylborate, sodium tetraphenylborate, sodium bis(2,2'-biphenylene)borate, potassium tetraphenylborate, tetramethylammonium tetraphenylborate, tetra-n-butylammonium tetraphenylborate, tetramethylphosphonium tetraphenylborate, tetra-n-butylphosphonium tetraphenylborate and tetraphenylphosphonium tetraphenylborate. The preferred catalysts within this class are the tetra-n-alkylammonium and tetra-n-alkylphosphonium tetraphenylborates. Tetramethylammonium tetraphenylborate is particularly preferred because of its high activity, relatively low cost and ease of preparation from tetramethylammonium hydroxide and an alkali metal tetraphenylborate.

Another class of particularly useful basic catalysts is disclosed in copending, commonly owned application Ser. No. 941,901, filed Dec. 15, 1986, now U.S. Pat. No. 4,701,519, the disclosure of which is also incorporated by reference herein. It comprises polymers containing alkali metal phenoxide and especially lithium phenoxide moieties. They are usually present as end groups, especially on linear polycarbonates having a number average molecular weight in the range of about 8,000–20,000 as determined by gel permeation chromatography relative to polystyrene. Such catalysts may be produced by reacting a suitable polymer with an alkali metal base, typically at a temperature in the range of about 200°–300° C.

The Lewis acids useful as polycarbonate formation catalysts are selected from non-halide compounds and include dioctyltin oxide, triethanolaminetitanium isopropoxide, tetra(2-ethylhexyl) titanate and polyvalent metal (especially titanium and aluminum) chelates such as bisisopropoxytitanium bisacetylacetonate (commercially available under the trade name "Tyzor AA") and the bisisopropoxyaluminum salt of ethyl acetoacetate.

The conversion of cyclic oligomers to crosslinked polymers is illustrated by the following example.

EXAMPLE 5

A solution in methylene chloride of the product of Example 4 and tetramethylammonium tetraphenylborate in the amount of 0.1 mole percent, based on carbonate units in said product, was rotoevaporated to produce an intimate cyclicscatalyst mixture. The mixture was heated at 250° C. for 2 hours. There was obtained a crosslinked polycarbonate which was 99.1% insoluble in methylene chloride and which had a glass transition temperature of 175° C.

Linear polycarbonates of the present invention, incorporating structural units of formula V, may be crosslinked by reaction with a polycarbonate formation catalyst under conditions similar to those described hereinabove with reference to cyclic oligomers.

What is claimed is:

1. A polycarbonate comprising cyclic carbonate structural units of the formula

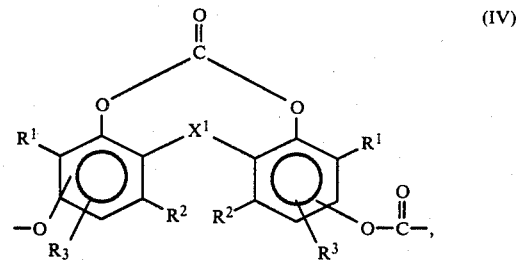

wherein:
$X^1$ is $R^3CH$, S, SO or $SO_2$;
$R^1$ is $C_{1-4}$ alkyl or halo;
each of $R^2$ and $R^4$ is independently hydrogen, $C_{1-4}$ alkyl or halo; and
$R^3$ is hydrogen or an alkyl, cycloalkyl or aryl radical.

2. A polycarbonate according to claim 1 which additionally comprises structural units of the formula

wherein $A^1$ is a divalent aromatic radical.

3. A polycarbonate according to claim 2 wherein $A^1$ has the formula $$-A^2-Y-A^3- \qquad (VI)$$

wherein each of $A^2$ and $A^3$ is a monocyclic divalent aromatic radical and Y is a bridging radical in which one or two atoms separate $A^2$ from $A^3$.

4. A polycarbonate according to claim 3 wherein the cyclic carbonate structural units have the formula

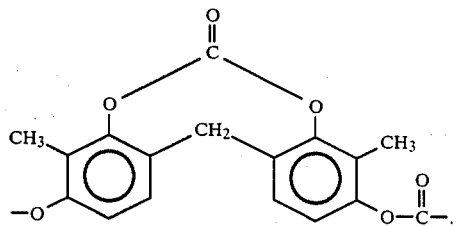

5. A polycarbonate according to claim 3 wherein the cyclic carbonate structural units have the formula

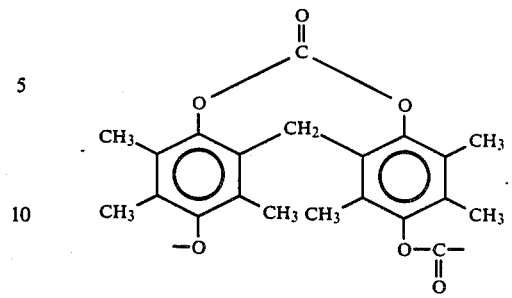

6. A polycarbonate according to claim 3 which is a linear polycarbonate.

7. A polycarbonate according to claim 3 which comprises at least one cyclic polycarbonate oligomer.

8. A method for the preparation of a crosslinked resinous composition which comprises contacting a polycarbonate according to claim 1 with a polycarbonate formation catalyst at a temperature up to about 350° C.

9. A method according to claim 8 wherein the polycarbonate formation catalyst is a base or a Lewis acid.

10. A crosslinked resinous composition prepared by the method of claim 8.

* * * * *